United States Patent [19]

Merkatoris et al.

[11] Patent Number: 5,190,606
[45] Date of Patent: Mar. 2, 1993

[54] METHOD FOR PRODUCING RAISED LEG CUFF FOR DIAPERS INCLUDING TWO FOLDING BOARDS

[75] Inventors: John R. Merkatoris, Green Bay; William Van Ryzin, De Pere, both of Wis.

[73] Assignee: Paper Converting Machine Company, Green Bay, Wis.

[21] Appl. No.: 715,905

[22] Filed: Jun. 14, 1991

[51] Int. Cl.$^5$ .............................................. B31D 5/04
[52] U.S. Cl. ..................................... 156/164; 156/204; 156/227; 156/229; 156/256; 156/324
[58] Field of Search ............... 156/200, 204, 164, 229, 156/161, 213, 227, 256, 299, 324; 604/385.2, 385.1, 358

[56] References Cited

U.S. PATENT DOCUMENTS

| | | | |
|---|---|---|---|
| 3,860,003 | 1/1975 | Buell | 604/385.2 |
| 4,488,927 | 12/1984 | Hooper | 156/464 |
| 4,695,278 | 9/1987 | Lawson . | |
| 4,704,115 | 11/1987 | Buell | 604/385.2 |
| 4,738,677 | 4/1988 | Foreman | 604/385.2 |
| 4,795,454 | 1/1989 | Dragoo | 604/385.2 |
| 4,816,025 | 3/1989 | Foreman | 604/385.2 |
| 4,834,740 | 5/1989 | Suzuki et al. | 156/164 X |
| 4,900,384 | 2/1990 | Sanders et al. | 156/200 X |
| 5,030,303 | 7/1991 | Cucuzza | 156/164 |
| 5,064,489 | 11/1991 | Ujimoto et al. | 156/164 |

Primary Examiner—Jeff H. Aftergut
Attorney, Agent, or Firm—Tilton, Fallon, Lungmus & Chestnut

[57] ABSTRACT

A method and apparatus for producing raised leg cuffs for diapers in which an elastic band is oriented in a straight line direction so as to be adhesively encapsulated between the fold portions of a diaper web while the same is passing through a folding board.

9 Claims, 2 Drawing Sheets

METHOD FOR PRODUCING RAISED LEG CUFF FOR DIAPERS INCLUDING TWO FOLDING BOARDS

BACKGROUND AND SUMMARY OF INVENTION:

This invention relates to a method and apparatus for producing a raised leg cuff for diapers and, more particularly, the method and apparatus for introducing an elastic band into the cuff in encapsulated condition while passing through a folding board. Cuffed diapers are well established in the disposable trade as exemplified by Pat. No. 4,695,278.

In the past, folding boards have only been used for folding webs (typically facial tissue), but now we are folding preglued webs and drawing elastic and/or barrier webs into the fold right at the folding board. This is a very simple solution to the problem of handling and assembling multiple webs with widely different tensions (i.e., the elastic has between 50% and 400% stretch).

The reverse C-fold developed by the folding boards rolls the parent web around the board to bring the mating surfaces together without sliding relative to each other. This allows the glue to "ride along" without causing wrinkles or glue buildup problems. Another advantage is that the other items assembled into the cuff can take a straight web path into the folded area thus eliminating the need to run the high tension members over turning surfaces (keeps them separated from the folding process).

According to the instant invention, we are able to install a tensioned elastic band within a cuff formed by longitudinally folding a web without subjecting the tensioned elastic band to change in direction whereby a positive positioning of the band relative to the thus folded cuff is developed.

Other objects and advantages of the invention may be seen in the details of the ensuing specification.

BRIEF DESCRIPTION OF THE DRAWINGS

The invention is described in conjunction with the accompanying drawings, in which.

DETAILED DESCRIPTION

Figure 3:
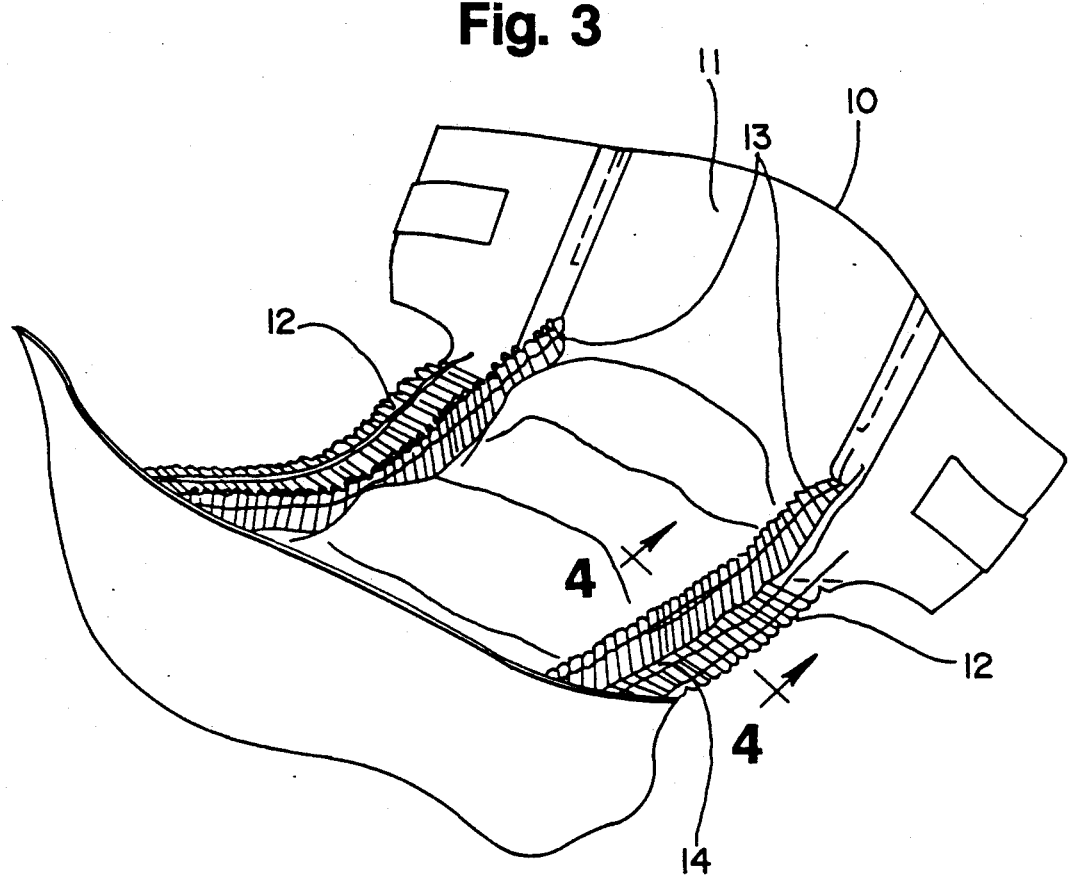
FIG. 3 is a perspective view of a diaper equipped with a raised leg cuff.

With reference to FIG. 3 the numeral 10 designates generally a disposable diaper which, in conventional fashion, includes superposed layers of moisture impervious web such as polyethylene, absorbent fluff layer and a nonwoven layer as at 11 which is in contact with the infant's body. The diaper 10 normally is equipped with elastic leg bands as at 12 which may be either outboard (as shown) or inboard of he raised leg cuffs 13. The raised leg cuff 13 can be seen in sectional view in FIG. 4 where there is a foot-like portion 14 attached to the nonwoven layer 11 and an upstanding portion 15 which is folded on itself as at 16 to confine one or more elastic boards 17. In the illustration given, the fold developed at 18 is positioned between two strips of adhesive as at 19 and 20 and which serve to encapsulate the elastic bands 17.

Figure 1:
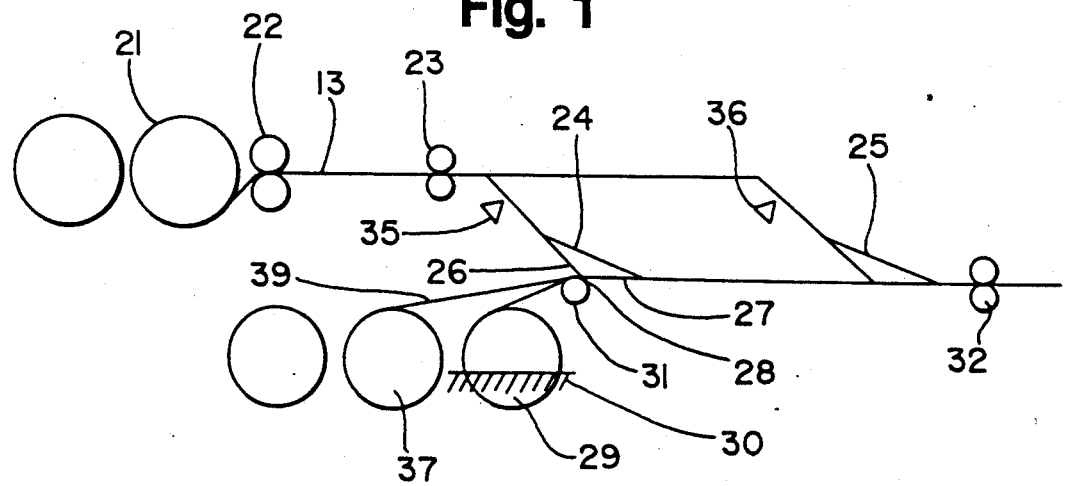
FIG. 1 is a schematic side elevational view of apparatus for practicing the invention.
Figure 4:
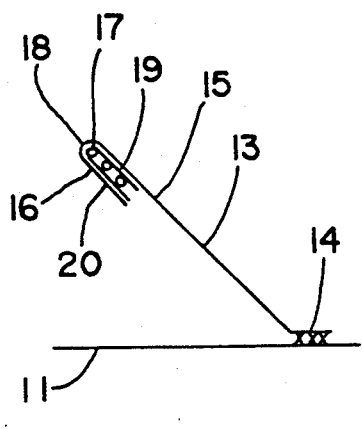
FIG. 4 is a sectional view taken along the sight line 4—4 as applied to FIG. 3.

The construction of FIGS. 3 and 4 is advantageously provided by the apparatus depicted schematically in FIG. 1. In FIG. 1 the numeral 21 designates a roll of nonwoven material to provide the two cuffs 13. For this purpose, the roll is twice as wide as each of and the web issuing therefrom is slit by a slitter mechanism as at 22. Thereafter, the two webs are pulled by means of pull rolls 23 along a generally longitudinally extending path which includes a folding board 24 for one web and 25 of the other web—one being a left hand folding board while the other is a right hand folding board.

Still referring to FIG. 1, each folding board is seen to have an upstream plate portion as at 26 and a downstream plate portion as at 27 developed by a transverse angle to provide the edge 28 which will be explained in further detail in conjunction with FIG. 2.

A roll 29 of elastic band material is operably associated with frame means 30 which may also support one or more of the previously described elements. The roll or elastic band material 29 is maintained in unwind means which includes a guide roll 31 which is seen to be aligned with the transverse angle 28 and also the downstream pull rolls 32 which are employed to advance the webs 13 through the folding boards at 24 or 25 as the case may be.

Figure 2:
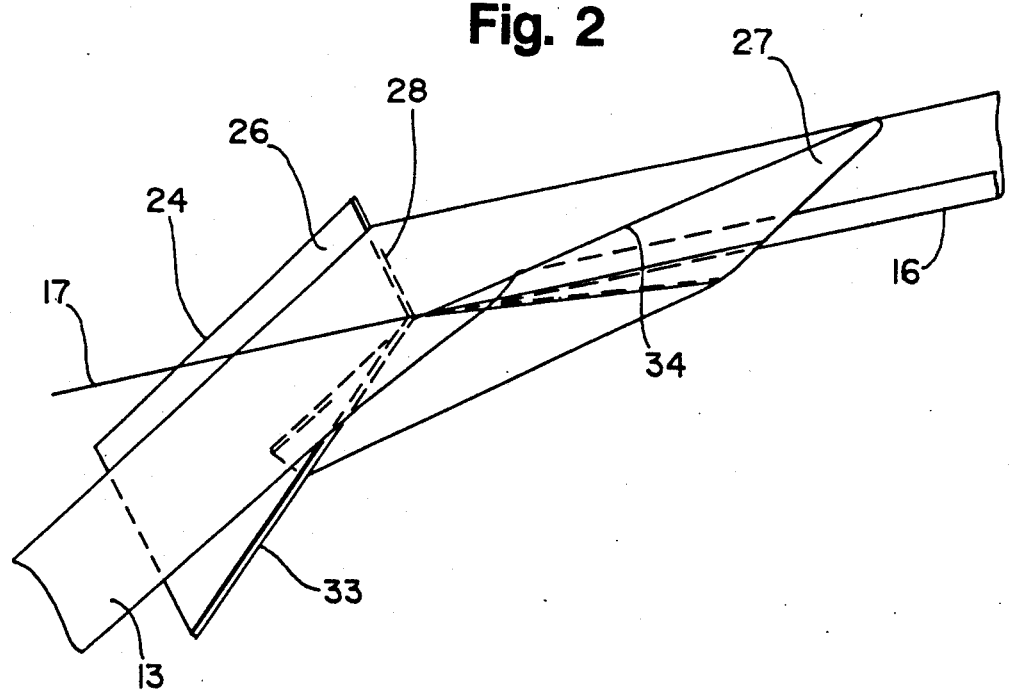
FIG. 2 is a perspective view as viewed from below of the folding board of FIG. 1 showing the interrelationship of the web and elastic band.

A reference is now made to FIG. 2 which is a perspective of the folding board 24 but as viewed from the underside so as to better appreciate the web orientation in developing the encapsulating fold for the elastic band. As before, the folding board 24 has an upstream plate portion 26 and a downstream plate portion 27. These are related so as to form the angle 28 in the web being advanced through the folding board.

As the web 13 is advanced through the folding board it encounters first an angled edge 33 on the upstream plate portion which starts to develop the reverse fold 16—as referred to in FIG. 4. Next, the web 13 encounters substantially simultaneously the angled edge 28 developed by the upstream and downstream plate portions 26, 27 and a third angled edge 34 provided by the downstream plate portion 27. This results in the longitudinal edge of the web being folded on itself to develop the overfold 16.

Meanwhile, the tensioned elastic band 17 has been introduced in between the portions 15, 16 of the fold and confined between the adhesive layers 19, 20 which may be advantageously applied by glue nozzles 35 relative to the web directed toward the folding board 24 or nozzles 36 relative to the web passing toward the folding board 25.

We have found it especially advantageous to provide adhesive on the two sides 15, 16 of the fold so as to achieve the advantageous encapsulation of the one or more elastic bands 17. Particularly in the case of a nonwoven web, the adhesive bonds quickly to the nonwoven but in its exposure after application it may not be sufficiently tacky to pick up the elastic band. However, when the elastic band is sandwiched between two layers of adhesive as at 19 and 20, there appears to be an attraction or an affinity of the adhesive layer for each other that quickly encapsulates the elastic band.

Figure 5:
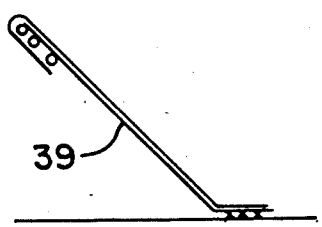
FIGS. 5 and 6 are views similar to FIG. 4 but showing alternative forms of leg cuff.

It is also possible through the practice of the invention to include the provision of the moisture impervious film as at 39 in FIG. 5—this being advantageously provided by a parent roll 37—see FIG. 1. The unwind means for the parent roll 37 also includes the guide roll 31 so that the unwind means for the moisture impervious film 39, the unwind means for the elastic band 17, the angle edge 28, and the pull rolls 32 are all colinear.

Figure 6:
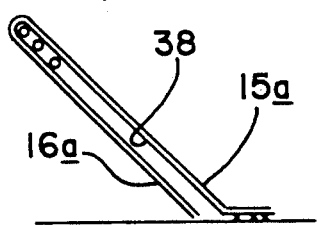

It is also within the purview of the invention to make use of an adhesive which has barrier-providing characteristics, i.e., being moisture impervious, through the use of a special adhesive as at 38 in FIG. 6. In this instance, the reverse fold portion 16 of FIG. 4 is elongated as at 16a in FIG. 6 so as to provide a portion of the nonwoven in full covering relation with the cuff portion 15a. This avoids exposing the adhesive to the infant's skin.

In summary, the forming board or plate used for the raised leg cuff is a reverse C-fold interfold board. The reverse C-fold allows the glue to be applied to the nonwoven so that the nonwoven can be folded without the glue coming in contact with the forming plate. The interfold part of the plat allows the elastic to be added in a straight line so no wrinkling is caused in the nonwoven. One or more strands of elastic can be added to the raised leg cuff. Polyethylene or other material can also be added by the straight line method of forming. Either glue as a barrier guard or polyethylene as water impermeable substance can be added to the leg cuff because of the ability to interfold other products into the nonwoven.

A small cuff can be added to a single liquid previous top sheet or the cuff can be made with a three piece liquid previous top sheet. There are many combinations of cuffs and cuff construction that can be made on this plate.

Some of the advantages of using this method to make raised leg cuffs are:

1. Gluing can be done by slot coating or swirl jet;
2. One or more strands of elasticated material can be added;
3. For the water impervious part of the product, either polyethylene or a water impervious glue can be used on this folding plate;
4. Small cuffs can be added to a continuous backsheet or a three piece backsheet could be made;
5. The width of a cuff is easily adjustable up to approximately ⅓ of the diaper width. The folded over portion of the cuff where the elastic is contained and can readily range from ¾" to 4-½";
6. The number of strands of elasticated material, the stretch given the strands and the placement widthwise of the strands is a very simple adjustment and can be made by a customer to change the looks of the diaper as desired.

We claim:

1. A method of forming a raised leg cuff for a diaper comprising:
   advancing first and second webs along a longitudinal path extending from unwind means toward first and second folding boards, respectively,
   applying a longitudinally extending strip of adhesive to each of said webs,
   applying a tensioned continuous elastic web to each of said webs in contact with said adhesive strip thereof,
   introducing the first and second webs equipped with said adhesive strips and elastic bands respectively into said first and second boards to roll a longitudinally extending fold in each web having confronting fold portions for encapsulating said elastic band within said adhesive strip, and to provide a longitudinally extending portion transversely spaced from said fold,
   advancing a third web along said path and adhering said portions of said first and second folded webs to said third web in transversely spaced relation to provide a diaper web having a pair of raised leg cuffs without additional folding or unfolding of any of said webs.

2. The method of claim 1 in which said adhesive strip is applied to each of said first and second webs relative to said longitudinally extending fold to position adhesive on both sides of said elastic band.

3. The method of claim 2 in which at least two transversely separated strips of adhesive are applied to each of said first and second webs with said fold being positioned between said strips.

4. The method of claim 1 in which said first and second folding boards includes a transverse angle defining an upstream plate portion and a downstream plate portion, and orienting the direction of said elastic bands so that said bands first contacts said first and second webs at about said transverse angle.

5. The method of claim 4 in which the orienting direction is parallel to and aligned with said downstream plate portion whereby said elastic bands extends in a straight line without encountering transverse change in direction until encapsulated in the first and second folding boards.

6. The method of claim 1 in which each of said first and second webs is equipped with a water impervious coating.

7. The method of claim 1 in which said first add second webs are adhered to inboard portions of said third web.

8. The method of claim 1 in which said first and second webs are adhered to side edge portions of said third web.

9. The method of claim 1 in which said first and second webs are slit from a single web in said path.

* * * * *